United States Patent [19]

Toussaint et al.

[11] 4,234,727
[45] Nov. 18, 1980

[54] PREPARATION OF AMINES

[75] Inventors: Herbert Toussaint, Frankenthal; Wolfgang Schroeder, Bad Durkheim; Wolfgang Franzischka, Ludwigshafen, all of Fed. Rep. of Germany

[73] Assignee: BASF Aktiengesellschaft, Fed. Rep. of Germany

[21] Appl. No.: 68,742

[22] Filed: Aug. 22, 1979

[30] Foreign Application Priority Data

Sep. 1, 1978 [DE] Fed. Rep. of Germany ....... 2838184

[51] Int. Cl.$^3$ ...................... C07C 85/06; C07C 85/08; C07D 241/04; C07D 295/02
[52] U.S. Cl. .................................... 544/178; 544/404; 546/184; 564/436; 564/462; 564/463
[58] Field of Search ............... 260/583 R, 577, 563 C; 544/178, 404; 546/184

[56] References Cited

U.S. PATENT DOCUMENTS

| | | | |
|---|---|---|---|
| 3,239,562 | 3/1966 | Barker | 260/563 C |
| 3,384,667 | 5/1968 | Hamilton | 260/585 B |
| 3,397,237 | 8/1968 | Jackson | 260/583 R |
| 3,520,933 | 7/1970 | Adam et al. | 260/585 C |
| 3,542,694 | 11/1970 | Schwettmann | 252/430 |
| 3,558,706 | 1/1971 | Hamilton | 260/577 |
| 3,976,697 | 8/1976 | Kuntschik et al. | 260/583 R |
| 4,014,933 | 3/1977 | Boettger et al. | 260/563 R |
| 4,036,883 | 7/1977 | Voges et al. | 260/585 B |
| 4,062,899 | 12/1977 | Laurer et al. | 568/855 |
| 4,138,437 | 2/1979 | Strauss et al. | 260/583 R |

FOREIGN PATENT DOCUMENTS

| | | | |
|---|---|---|---|
| 637731 | 11/1936 | Fed. Rep. of Germany | 260/583 R |
| 2445303 | 9/1974 | Fed. Rep. of Germany | 260/583 R |
| 1451777 | 10/1976 | United Kingdom | 260/585 B |

*Primary Examiner*—John Doll
*Attorney, Agent, or Firm*—Keil & Witherspoon

[57] ABSTRACT

Amines are N-alkylated by reaction with an alcohol or a carbonyl compound in the presence of hydrogen under atmospheric pressure in the gas phase over a catalyst, containing copper and aluminum, which is obtained by heating and reducing a basic precipitate of salts of copper and aluminum.

2 Claims, 1 Drawing Figure

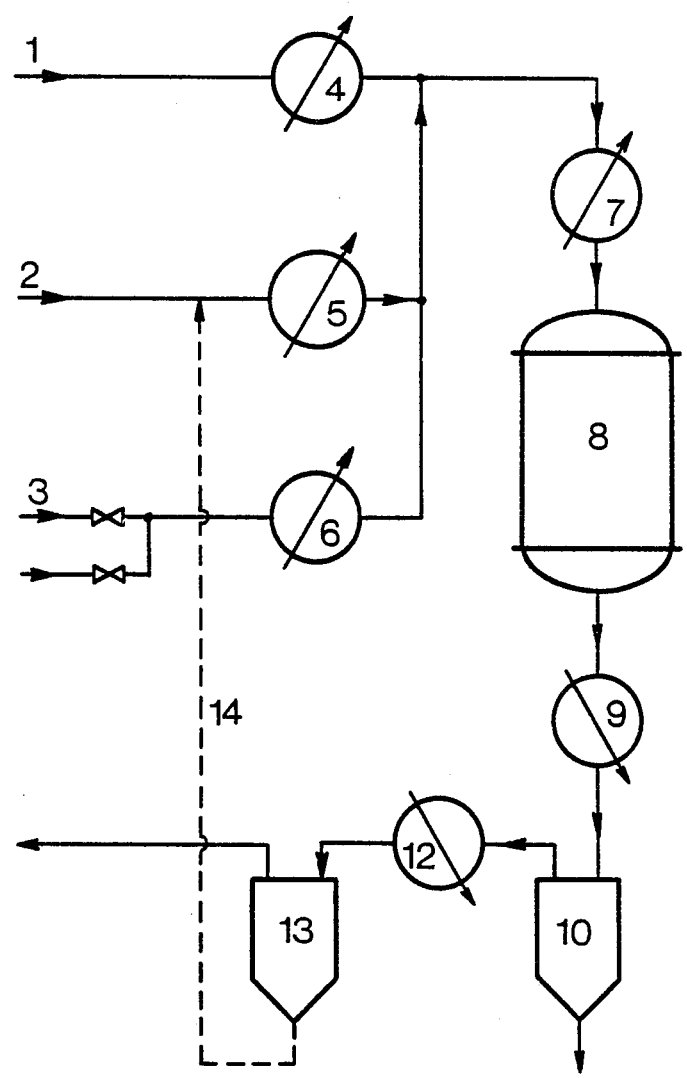

PREPARATION OF AMINES

The present invention relates to a process for the N-alkylation of amines, ie. for the preparation of secondary or tertiary amines by reacting primary or secondary amines with alcohols or carbonyl compounds in the gas phase under hydrogenating conditions.

Secondary and tertiary amines have many uses, for example as intermediates and acid neutralizers in various syntheses, as catalysts for the preparation of polyurethanes, and as bactericides.

A plurality of processes has been proposed for the preparation of substituted amines by alkylating incompletely substituted amines; these processes can be classified into groups:

One group of processes employs, as the catalysts, transition metals of group 8 of the periodic table, eg. nickel, especially Raney nickel, in the presence of hydrogen; occasionally, the platinum metals are also specified. The reactants are in general in the liquid phase, and less frequently in the gas phase; in many cases the process is carried out under atmospheric pressure.

Another group employs catalysts of the type of ADKINS copper-chromium oxide (copper chromite). For these, a pressure range of from 10 to 25 bar, and sometimes up to 200 bar or even higher, is usually employed, so that the reactants are always present in the liquid state.

German Pat. No. 881,657 also discloses a process in which the reactants are employed in the gaseous state. This process is carried out at from 10 to 15 bar and a relatively high temperature (from 240° to 300° C.).

In a third group of processes, the catalyst employed is an oxide possessing dehydrating properties, for example $Al_2O_3$ or $SiO_2$. These processes in some cases employ very high temperatures (up to 400° C.) and frequently also high pressures (up to 200 bar). Only in exceptional cases does such a process succeed if carried out under atmospheric pressure and in the gas phase (cf., for example, German Pat. No. 637,731 and U.S. Pat. No. 3,384,667).

The very fact that such different processes have been proposed leads to the conclusion that all of these processes suffer from some disadvantages:

The elements of group 8 can, because of their high hydrogenating activity, result in the loss of alkyl groups, already present, from the nitrogen of the amine, thereby favoring the formation of secondary and often even primary amines and (by trans-alkylation) the formation of other amines than those required.

The other processes are as a rule carried out under high pressure; this entails high energy consumption and material consumption and, if faults should develop, certain hazards.

It is an object of the present invention to provide a process for the N-alkylation of amines which is simple, employs cheap catalysts and gives a high yield.

We have found that this object is achieved if the reaction is carried out over certain copper-containing fixed bed catalysts at pressures under 10 bar, preferably under 5 bar, more especially at atmospheric pressure, and at below 300° C.

The copper catalysts used are those described in German Laid-Open Application DOS 2,445,303. They may be regarded as amorphous products of the thermal decomposition and reduction of basic copper-aluminum carbonates and may be obtained by precipitating dilute or moderately concentrated solutions, preferably less than 3-molar solutions, of salts of copper and aluminum with an alkali metal carbonate at pH 8–10 and decomposing the resulting precipitates, before or after suitable molding, at 350°–600° C. For details, reference may be made to the description given in the last-mentioned DOS. After conventional reduction, highly active catalysts which are extremely suitable for the present process are obtained.

The process is equally applicable to incompletely alkylated aliphatic amines and incompletely alkylated aromatic amines. These amines, which may be primary or secondary, can in particular be reacted with monohydric aliphatic alcohols, ranging from methanol to about tetra-decanol, at atmospheric pressure in the presence of hydrogen, the yield being virtually quantitative. In many cases, it is equally economical to use corresponding aldehyde and ketones; these in general have boiling points of up to 250° C. under atmospheric pressure.

Trans-alkylation reactions, and the formation of secondary or primary amines from tertiary or secondary amines respectively are only observed to a slight extent, if at all. The reactions can even be carried out in glass apparatus. If the equipment should leak for any reason, only small amounts of amines pass into the environment; furthermore, the probability of a leakage occurring at all is substantially less than with processes carried out under pressure.

The process can be carried out as follows: the reactor used is, for example, a vertical cylindrical vessel, preferably a vertical pipe bundle, with conventional devices for cooling and heating. It is filled with the catalyst according to the invention, which is molded to a shape conventionally used for industrial purposes, for example cylindrical tablets which are about 3 to 10 mm in height and/or width. The end faces of the cylinder may be plane, concave or convex. Catalyst shapes other than cylinders, for example spheres or elongate extrudates, may also be used. The catalyst may be introduced into the reactor either in a pre-reduced, passive state or in the oxide state. In the former case, it is reactivated by a brief treatment with a nitrogen-hydrogen mixture at 100°–150° C., whilst in the second case the entire reduction is carried out in the reactor. Thereafter, the reactor is brought to the requisite temperatures, which is in general from 100° to 250° C. At the same time, the hydrogen flow required for the reaction is set up; the hydrogen is preferably recycled and may flow upward or downward through the reactor. The amount of hydrogen is in general of the order of from 100 to 2,000 units of volume of hydrogen (measured under reaction conditions) per unit of volume of the catalyst per hour. If the partial pressure of hydrogen is too low, by-products may form and in the long run the activity of the catalyst may suffer. In most cases, a partial pressure of hydrogen of the order of from 0.3 to 0.8 bar suffices, and the reaction can be carried out at a total pressure equal to atmospheric pressure. If a partial hydrogen pressure of from 0.7 to 0.8 bar does not suffice, it may be necessary to work at slightly superatmospheric total pressure. Of course, the process also works entirely satisfactorily at higher pressures.

The stream of hydrogen is advantageously first brought to about 300°–400° C. in a preheater and is then utilized for vaporizing the reactants, which are fed as liquids to a vaporizer wherein they are entrained by the heated hydrogen. The resulting mixture flows through the reactor and is cooled, if appropriate, down to about −10° C. in a system of heat exchangers and coolers and, if necessary, is additionally compressed in order to cause condensable constituents to separate out. The hydrogen then returns to the preheater.

Particularly when using an excess of amine—which may be, for example, up to 20 moles per mole of alcohol—the mixture leaving the reactor contains, in addition to the reaction product, excess hydrogen and water, a corresponding amount of the original amine, whilst the alcohol or carbonyl compounds have in general been completely converted.

Thus, the separation of this mixture of compounds as a rule requires, additionally, to the cooling stage, a distillation stage in order to remove the unconverted amine, and a process for separating off the water or drying the product. This can equally be effected by distillation, but also, for example, by a treatment with concentrated sodium hydroxide solution.

It is of course also possible to carry out the reaction with an excess of alcohol or carbonyl compound, and the decision as to which procedure to follow is in general determined by economic considerations. If the reaction products have a high boiling point and the unconverted amine has a low boiling point, which is especially the case where a long-chain alcohol or long-chain carbonyl compound has been used in the reaction, the unconverted volatile amine can be recycled as a gas, together with the hydrogen, and merely be replenished to the extent that it has reacted.

For this reason the process is also particularly suitable for the reaction of alcohols or carbonyl compounds which have a high boiling point, which in some cases may even be above the reaction temperature. In these cases, particularly, it is advantageous to vaporize these high-boiling compounds by means of the recycled gas or gas mixture, ie., in the simplest case, to saturate the circulating gas with these compounds. In other cases also, this procedure facilitates vaporization, as has already been explained above.

EXAMPLE 1

Reaction of dodecyl alcohol with dimethylamine (compare FIGURE)

The reactor consists of a cylindrical vertical vessel (8) which can be heated by a circulating organic heat transfer medium, and which is filled with a catalyst in the form of cylinders of 3 mm height and 3 mm diameter; the catalyst has been prepared in accordance with Example 1 of German Laid-Open Application DOS 2,445,303. It is reduced at 120°–140° C. by first flushing the line (3) with nitrogen, to which subsequently from 3 to 5 percent by volume of hydrogen are added. When water starts to separate out more slowly, the temperature is gradually raised to 200° C. When the formation of water has ceased, the nitrogen is replaced by hydrogen. The gas flow rate is set to 570 parts by volume (S.T.P.) per hour per unit volume of catalyst. The hydrogen is preheated to about 250° C. in the heat exchanger (6). Through line (2), 28 parts by volume (S.T.P.) per hour of gaseous dimethylamine, which has been preheated to about 250° C. in the heat exchanger (5), are added to the stream of hydrogen.

Commercial dodecyl alcohol, which, according to gas chromatography, contains about 1.4 percent (assessed on area) of constituents with shorter retention time is used for the reaction. Per hour, 0.1 part by volume of liquid alcohol, corresponding to a molar ratio of dimethylamine to dodecanol of 1.3:1, is fed through line (1) and through the heat exchanger (4) to the gas mixture and then to the vaporizer (7). It is completely vaporized at about 200° C. The resulting gas mixture enters the reactor under a pressure of about 1.1 bar. The reaction is conducted so as to give a maximum temperature of 170° C. The hottest point is approximately between the 1st and the 2nd quarter of the catalyst bed, viewed in the direction of flow. The temperature drops by about 10° C. near the reactor exit. In the cooler (9), the reaction mixture is cooled to room temperature. The condensate collects in the separator (10). It has the following composition according to gas chromatography:

Dimethyldodecylamine: 97.0%
Dimethylamine: 0.6%
Monomethyldodecylamine 0.3%
Water (according to K. Fischer): 0.9%
Other constituents: 1.2%

Unconverted dodecanol and other high-boiling constituents are not found.

EXAMPLE 2

Reaction of piperidine with methanol

The equipment described in Example 1 is used. 120 parts by volume (S.T.P.) of hydrogen per part by volume of catalyst per hour are passed through at a maximum reaction temperature of 180° C. The preset temperature in the vaporizer (7) is 250° C. A mixture of piperidine and methanol in the molar ratio of 1:4, and in an amount corresponding to 0.2 part by volume in the liquid state is fed to the stream of hydrogen. The condensate obtained has the following composition, according to gas chromatography:

N-Methylpiperidine: 79.3%
Piperidine: —
Methanol: 19.4%
Remainder: 1.3%

EXAMPLE 3

Reaction of cyclohexanone with dimethylamine

The equipment described in Example 1 is used. The mean reaction temperature is 140° C. and a stream of hydrogen of 60 parts by volume (S.T.P.) per hour per part by volume of catalyst is used. The temperature in the heat exchanger (6) and in the vaporizer (7) is also 140° C. 20 parts by volume (S.T.P.) of gaseous dimethylamine are fed in per hour per part by volume of catalyst through lines (2) and the heat exchanger (5). Liquid cyclohexanone in an amount of 0.03 part by volume of liquid per hour per part by volume of catalyst is introduced through lines (1) and the heat exchanger (4), where it vaporizes. The maximum temperature measured in the reactor is 160° C. The reaction mixture is cooled to room temperature and is found, by gas chromatography, to have the following composition (excluding water):

Dimethylcyclohexylamine: 89%
Dimethylamine: 8%
Cyclohexanol: 1%
Remainder: 2%

EXAMPLE 5

Reaction of ethanol with dimethylamine

The procedure described in Example 1 is followed. 60 parts by volume of hydrogen are introduced per hour per part by volume of catalyst via the heat exchanger (6) and the vaporizer (7), the temperature of each being set to 150° C. 20 parts by volume (S.T.P.) per hour per part by volume of catalyst of gaseous methylamine are passed through the heat exchanger (5), which is also set to 150° C. and then admixed to the stream of hydrogen, whilst 0.1 part by volume of liquid ethanol per hour per part by volume of catalyst is introduced into the gas stream via the heat exchanger (4) and vaporizes completely in the vaporizer (7). After leaving the reactor, the reaction mixture is cooled in 2 stages; the fraction obtained at room temperature has the following composition (excluding water):

Dimethylethylamine: 49%
Ethanol: 48%
Remainder: 3%

In a second cooler (12), the residual gas is cooled to −40° C., as a result of which a low temperature condensate having the following composition is obtained in the vessel (13):

Dimethylethylamine: 90%
Ethanol: 6%
Dimethylamine: 2%
Remainder: 2%

This condensate is formed in an amount of 14%, based on the total condensable amount of constituents, and is recycled to the reactor (as shown schematically by the broken line (14) in the FIGURE).

EXAMPLE 5

To obtain N-n-propylaniline, a mixture of 0.35 part by volume of liquid aniline and propanol, in the molar ratio of 1:1.1, is fed per hour (per part by volume of catalyst) to the reactor described in Example 1, by taking up the mixture, in the vaporizer, in a stream of hydrogen (120 parts by volume (S.T.P.) per hour per part by volume of catalyst) which has been preheated to 200° C. The pressure at the reactor inlet is 1.1 bar; the temperature in the reactor is not allowed to exceed 190° C. The condensate collected in the separator forms an aqueous layer and an organic layer; the latter consists of 89% of N-n-propylaniline, 4% of propanol, 4% of aniline and 3% of other constituents.

EXAMPLE 6

N-Ethyltoluidine is prepared from o-toluidine and ethanol by a method similar to that described in Example 5. The amount of hydrogen is 150 parts by volume (S.T.P.) and the mixture of starting materials amounts to 0.5 part by volume of liquid. A mixture of 80% of N-ethyl-o-toluidine, 2% of N,N-diethyl-o-toluidine, 13% of o-toluidine, 4% of ethanol and 1% of other constituents is obtained.

OTHER EXAMPLES

Examples of other compounds which were obtained equally successfully to those described above are N,N-dimethylpiperazine from methanol and piperazine, N-laurylmorpholine from morpholine and lauryl alcohol and N,N-di-n-butylaniline from N-butyraldehyde and N-n-butylaniline. For reactions with methanol, the temperature should not exceed 170° C., to avoid decomposition of the methanol to $CO+H_2$.

We claim:

1. A process for N-alkylating an amine by reacting it with an alcohol or carbonyl compound in the gas phase over a copper catalyst under hydrogenating conditions, wherein the reaction is carried out over a copper catalyst which has been obtained by thermal decomposition and reduction of a basic copper-aluminum carbonate.

2. A process as claimed in claim 1, wherein the copper catalyst used is obtained by precipitating a dilute or moderately concentrated solution of salts of copper and aluminum with an alkali metal carbonate at pH 8–10, decomposing the resulting precipitate, after appropriate molding, at 350°–600° C., and reducing the product in the conventional manner.

* * * * *